United States Patent [19]

Podszun et al.

[11] Patent Number: 5,395,737
[45] Date of Patent: Mar. 7, 1995

[54] HEAT- AND PHOTO-SENSITIVE IMAGING ELEMENT AND METHOD FOR MAKING IMAGES THEREWITH

[75] Inventors: Wolfgang Podszun, Cologne, Germany; Herman J. Uytterhoeven, Bonheiden, Belgium; Michael Müller, Bergisch Gladbach, Germany

[73] Assignee: Agfa-Gevaert, N.V., Mortsel, Belgium

[21] Appl. No.: 99,440

[22] Filed: Jul. 30, 1993

[30] Foreign Application Priority Data

Aug. 11, 1992 [EP] European Pat. Off. ............ 92202465

[51] Int. Cl.⁶ .................................................. G03C 1/73
[52] U.S. Cl. ................................... 430/284; 430/283; 430/288; 430/292; 430/332; 430/336; 430/338
[58] Field of Search ............... 430/284, 288, 338, 332, 430/292, 336, 283; 500/200, 201

[56] References Cited

U.S. PATENT DOCUMENTS

| | | |
|---|---|---|
| 3,954,584 | 5/1976 | Miyata et al. ....................... 430/284 |
| 4,019,972 | 4/1977 | Faust ................................... 430/288 |
| 4,065,315 | 12/1977 | Yamazaki et al. .................. 430/288 |
| 4,529,681 | 7/1985 | Usami et al. ........................ 430/138 |
| 4,702,997 | 10/1987 | Ai et al. ............................... 430/325 |
| 4,857,438 | 8/1989 | Loerzer et al. ..................... 430/332 |
| 4,886,735 | 12/1989 | Boettcher et al. .................. 430/332 |
| 5,292,610 | 3/1994 | Helling et al. ...................... 430/138 |

FOREIGN PATENT DOCUMENTS 1379228  1/1925  United Kingdom .

Primary Examiner—Charles L. Bowers, Jr.
Assistant Examiner—John A. McPherson
Attorney, Agent, or Firm—Breiner & Breiner

[57] ABSTRACT

An imaging element is disclosed comprising on a support a dye precursor and a color developer arranged in the same layer or in separate layers characterized in that a specific type of monomers according to one of formulas (I) or (II) and a photoinitiator is present in a layer containing said dye precursor and/or color developer. The imaging element of the invention can used as photosensitive as well as heat-sensitive imaging element for obtaining an image.

12 Claims, No Drawings

HEAT- AND PHOTO-SENSITIVE IMAGING ELEMENT AND METHOD FOR MAKING IMAGES THEREWITH

DESCRIPTION

1. Field of the Invention

The present invention relates to an imaging element that can be imaged by means of heat or that can be imaged by exposure to an image-wise pattern of actinic radiation.

2. Background of the Invention

Heat sensitive recording materials are well known and generally offer more convenience than other imaging systems besides an ecological advantage. Among heat sensitive recording materials there are known, thermal transfer system in which an image forming substance e.g. a dye is image-wise transferred from a donor element to a receiving element upon the application of heat, heat mode recording materials in which a heat pattern cause a change in e.g. the adhesion of an image forming substance which can subsequently employed to develop the image, recording materials where upon exposure with a powerful laser parts of an image forming layer are burned away or destroyed etc.

A further well known heat sensitive recording material is based on a reaction between a dye precursor and a color developer that can be initiated by the application of heat. Generally the dye precursor is a leuco dye and the color developer an organic acid or phenolic compound. In order to prevent premature color formation the leuco dye and color developer are arranged in separate layers or they can be both contained in one binder layer. In the latter case the binder is choosen such that its softening temperature is well above ambient temperature and image-wise heating the binder layer will then cause local softening of the binder so that reaction between the dye precursor and developer can take place.

Heat sensitive recording materials based on leuco dyes are very easy in use and are employed in e.g. teleprinters, facsimiles, in recording and measuring instruments etc. However, since leuco dye and color developer remain present in unreacted form in the non-image areas of the image the long term storage stability of the image is poor. Attempts have been made to improve the stability of the image by adding certain compounds as disclosed in e.g. U.S. Pat. No. 4,473,831 and EP-A-252691 or by using specific developers as disclosed in e.g. U.S. Pat. No. 4,531,139 and EP-A-269443.

SUMMARY OF THE INVENTION

It is an object of the present invention to provide an imaging element that can be employed as a heat sensitive recording element or as a light sensitive recording element and that yields images of improved stability.

It is another object of the present invention to provide a method for obtaining images with the above defined imaging element.

Further objects will become clear from the description hereinafter.

According to the present invention there is provided an imaging element comprising on a support a dye precursor and a color developer arranged in the same layer or in separate layers characterized in that a monomer according to one of formulas (I) or (II) and a photoinitiator is present in a layer containing said dye precursor and/or color developer:

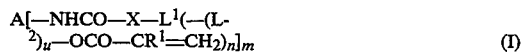

(I)

wherein n represents an integer from 1 to 3, m equals an integer of 3 to 6 when n equals 1, and 2 to 6 when n equals 2 or 3, and u equals 0 or 1; A represents an organic group of the following nature being 3 to 6 valent when n equals 1 and being 2 to 6 valent when n equals 2 or 3:

a) a hydrocarbon residue containing 5 to 25 carbon atoms which may be interrupted by one or more ether, ester or amide functions;

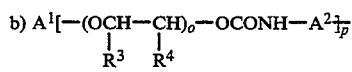

with $A^1$ representing a linear or branched aliphatic residue that may contain 0 to 3 0-atoms and 2 to 20 C-atoms, an aromatic residue containing 6 to 24 carbon atoms, an aromatic aliphatic residue containing 7 to 28 C-atoms or an cycloaliphatic residue containing 6 to 26 C-atoms, $R^3$ and $R^4$ each independently representing a hydrogen or a methyl group, $A^2$ representing an aromatic, aliphatic or cycloaliphatic hydrocarbon residue containing 5 to 25 carbon atoms, o represents an integer of 0 to 5 and p represents an integer of 2 to 6 when n equals 2 or 3 and represents an integer of 3 to 6 when n equals 1;

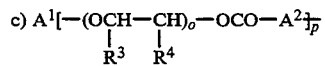

wherein $A^1$, $A^2$, $R^3$, $R^4$, o and p have the same meaning as defined above

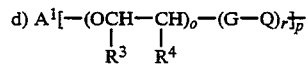

wherein $A^1$, $R^3$, $R^4$, o and p have the same meaning as defined above;

G represents $-O-CO-NH-Y(-COO-)_q-$;
wherein Y represents a divalent (cyclo)aliphatic residue containing 2 to 15 C-atoms and that may contain an ester, ether or urethane function, and q represents 0 or 1

Q represents a linear or branched aliphatic hydrocarbon residue containing 3 to 15 carbon atoms and which may comprise 1 to 3 oxygen bridges and r equals 0 or 1, X represents 0 or $NR^2$, $L^1$ represents an aliphatic hydrocarbon residue that is at least divalent and that may comprise 1 to 3 0-atoms, $L^2$ represents a lower alkylene of 1 to 6 C-atoms which may be branched or linear, $R^1$ represents hydrogen or a methyl group, $R^2$ represents hydrogen or a lower alkyl group of 1 to 6 C-atoms;

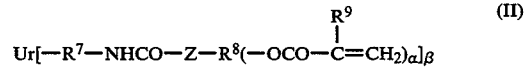

(II)

wherein

Ur represents a divalent or trivalent condensed urea residue;

Z represents O or $NR^{10}$ with $R^{10}$ representing alkyl containing 1 to 12 C-atoms;

$R^7$ represents a divalent hydrocarbon residue containing 2 to 25 C-atoms;

$R^8$ represents a hydrocarbon residue with a valence between 2 and 6, and containing 2 to 18 C-atoms, which can be linear or branched and which can be interrupted by up to 3 0 atoms;

$R^9$ represents hydrogen or methyl;

α represents an integer from 1 to 5, and

β equals 2 or 3.

According to the present invention there is also provided a method for obtaining images with the above defined imaging elements.

DETAILED DESCRIPTION OF THE INVENTION

It has been found that by incorporating a monomer according to formula (I) or (II) in a layer containing a dye precursor and/or a color developer and a photoinitiator an imaging element is obtained that can be imaged according to one of the following methods:

According to a first method said imaging element is image-wise exposed to actinic radiation thereby causing polymerization of the monomer in the exposed part so that as a consequence the dye precursor and/or color developer are immobilized (or the diffusion of said compound(s) is at least substantially decreased) at these parts. The imaging element is then overall heated thereby causing reaction of the dye precursor and color developer in the non-exposed areas so that a color develops in the areas.

According to a second method said imaging element is image-wise exposed by heat thereby causing color formation in the exposed areas and subsequently overall exposing said imaging element to actinic radiation so that the unreacted dye precursor and color developer are immobilized or the diffusion thereof is substantially decreased.

Image-wise exposure by actinic radiation or heat and overall exposure to respectively heat or actinic radiation in the above methods can also be carried out simultaneously in accordance with the present invention.

The exposure to actinic radiation can be a contact exposure using e.g ultraviolet radiation, a camera exposure, a scanning exposure, or a laser exposure. The radiation source used in carrying out the exposure step includes e.g. sunlight, incandescent lamps, mercury vapour lamps, halogen lamps, xenon lamps, fluorescent lamps, light-emitting diodes, lasers, electron rays, and X-rays.

Exposure of the imaging element to heat can be carried out by e.g. a thermal head, as e.g. in a thermal printer or by a laser. In the latter case the imaging element will preferably include a substance that is capable of converting the laser light to heat and the wavelength of the laser will be selected such that it will not cause polymerization of the monomer in according to formula (I) and/or (II). In case of an overall exposure the heat can also be applied by guiding the element through a pair of rolls at least one of which is at an elevated temperature.

The images obtained according to one of the methods described above show an improved stability due to efficient immobilization of unreacted dye precursor and color developer. Further a high light sensitivity of the imaging element was found.

Preferably used monomers in an imaging element according to the invention comprise one of the following residues as hydrocarbon residue A and/or $A^2$ of general formula (I):

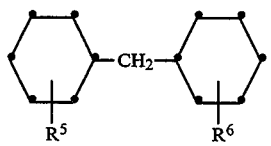
Ia

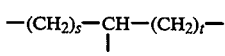
Ib

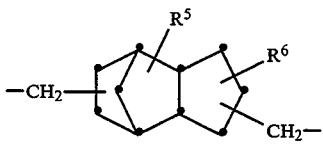
Ic

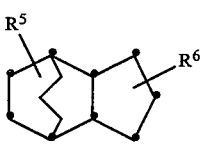
Id wherein $R^5$ and $R^6$ each independently represent hydrogen or a lower alkyl of 1 to 6 C-atoms, s and t independently represent an integer from 1 to 6 and wherein the aliphatic hydrocarbon residues Ia, Ic and Id comprise 2 to 6 free valences.

Examples of monomers according to formula (I) suitable for use in accordance with the present invention are shown in table 1.

TABLE 1

| | |
|---|---|
| $CH_3-CH_2-C[CH_2O-(CH_2CH-O-)_{2.4}-CO-(CH_2)_5-NHCOO-CH_2-CH_2-O-CO-C=CH_2]_3$ with $CH_3$ branches on both sides | 1 |
| $CH_3-CH_2-C[CH_2O-(CH_2CH-O-)_{2.4}-CO-(CH_2)_5-NHCOO-CH-(CH_2-O-CO-C=CH_2)_2]_3$ with $CH_3$ branches on both sides | 2 |
| $C[CH_2O-CO-(CH_2)_5-NH-COO-CH_2-CH_2-OCO-CH=CH_2]_4$ | 3 |
| $C[CH_2O-CO-(CH_2)_5-NH-COO-CH_2-CH_2-OCO-C=CH_2]_4$ with $CH_3$ branch | 4 |

TABLE 1-continued

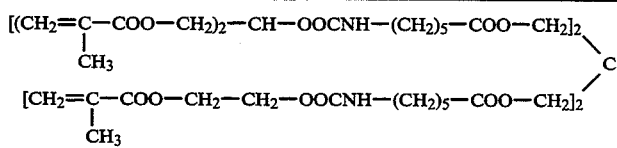  5

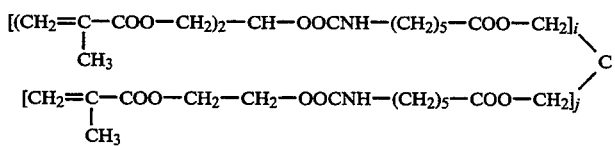  6 i and j are respectively 3.5 and 0.5 indicating that compound 6 is a mixture of compounds obtained by reacting i equivalents of glycerine-dimethacrylate and j equivalents of hydroxyethyl methacrylate as disclosed in DE 3,703,130.

i and j are respectively 2.5 and 1.5 indicating that compound 7 is a mixture of compounds obtained by reacting i equivalents of glycerine-dimethacrylate and j equivalents of hydroxyethyl methacrylate as disclosed in DE 3,703,130.

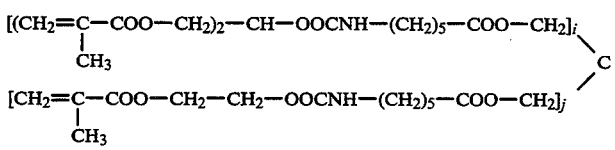  7

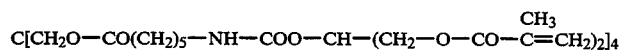  8

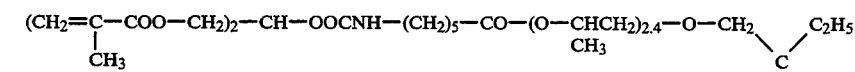  9

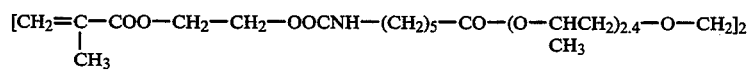

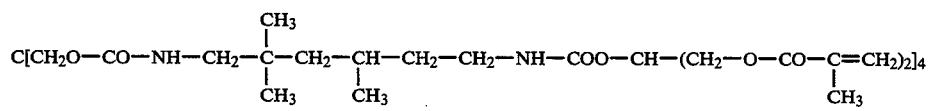  10

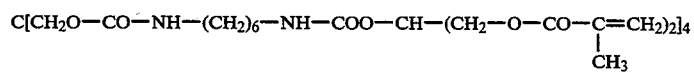  11

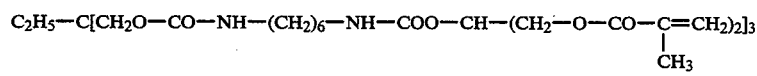  12

C₂H₅—C[CH₂O—CO—NH—(CH₂)₆—NH—COO—CH—(CH₂—O—CO—C(CH₃)=CH₂)₂]₃  13

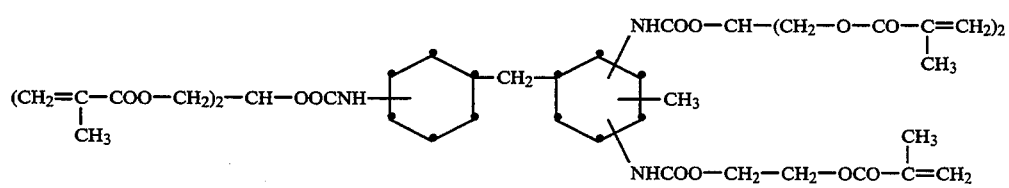  14

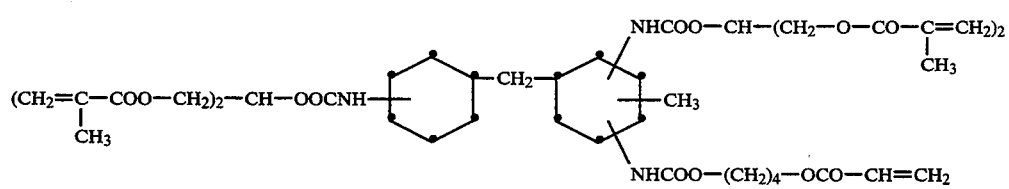  15

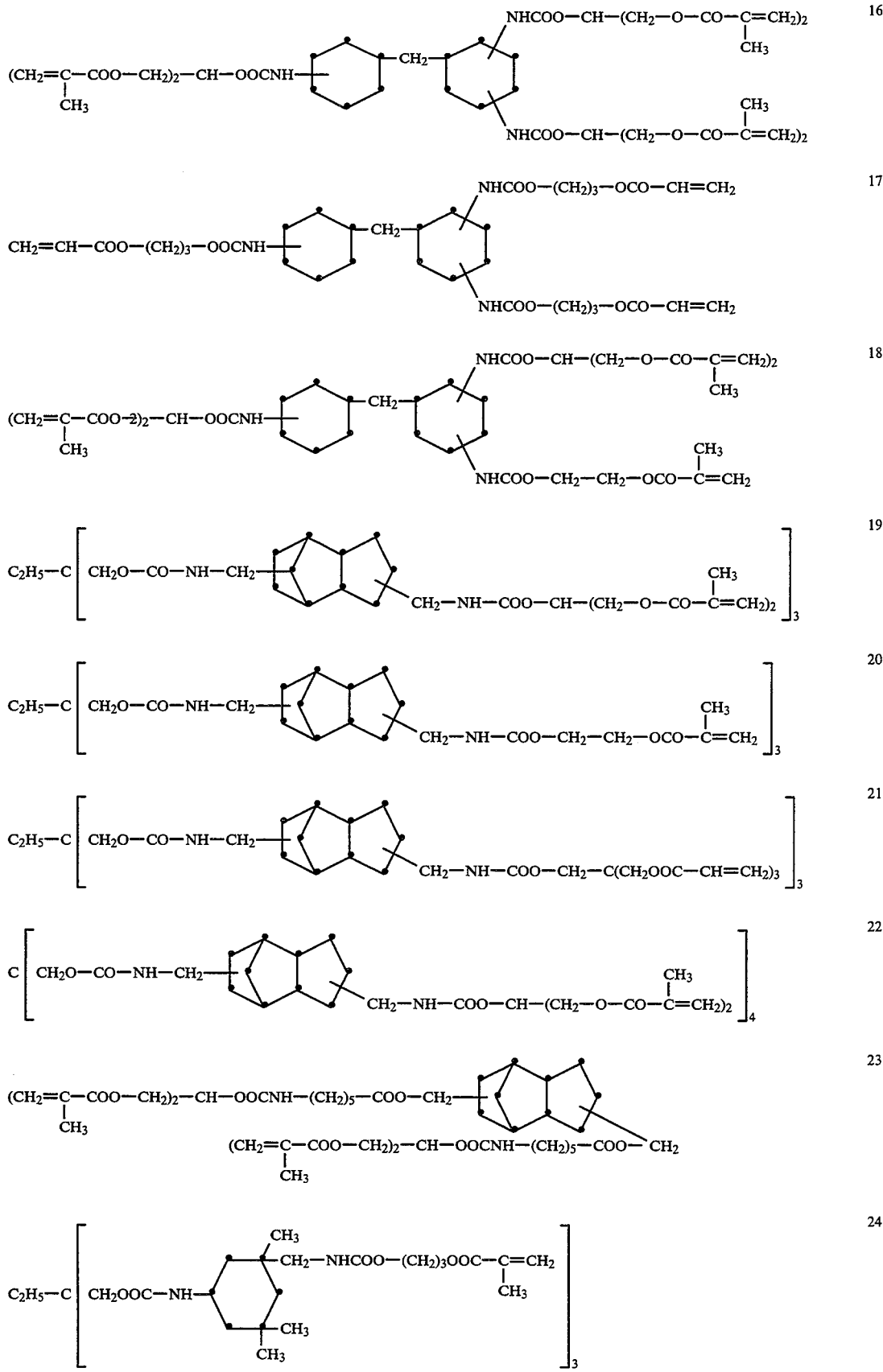

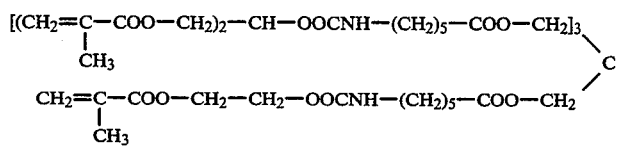

The fractal indexes in the formulas 1, 2 and 10 indicate that these formulas represent a mixture of compounds having a different length of the ethylene-oxide piece in said formulas the indexes thus representing an average of said ethylene-oxide piece. The formulas 14 to 23 represent a mixture of structural isomers and can be used in accordance with the present invention without separation of the isomers.

The monomers corresponding to general formula (I) are known and can be prepared according to the German patent application numbers 3,522,005, 3,703,080, 3,643,216, 3,703,130, 3,917,320 and 3,743,728.

In general formula (II) preferred condensed urea residues represented by Ur are following structural units:

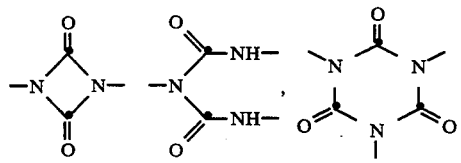

Preferably the divalent residue represented by Z is an oxygen atom. In the case Z represents $NR^{10}$, then $R^{10}$ is preferably a linear or branched alkyl group, e.g. methyl, ethyl, propyl or t.butyl.

The hydrocarbon residue represented by $R^7$ may be interrupted by oxygen. $R^7$ represents aliphatic, aromatic or mixed aliphatic-aromatic hydrocarbon residues. For example, $R^7$ equals a divalent linear or branched aliphatic group, preferably having 2 to 12 carbon atoms, e.g. ethylene, propylene, 1,4-tetramethylene, 1,6-hexamethylene and 2,2,4-trimethyl-1,6-hexamethylene and their isomers. Alternatively $R^7$ may represent a monocyclic or polycyclic saturated or aromatic hydrocarbon residue having 6 to 24, and preferably 6 to 14 carbon atoms.

Examples of preferred useful monomers according to general formula (II) are listed below in table 2:

TABLE 2

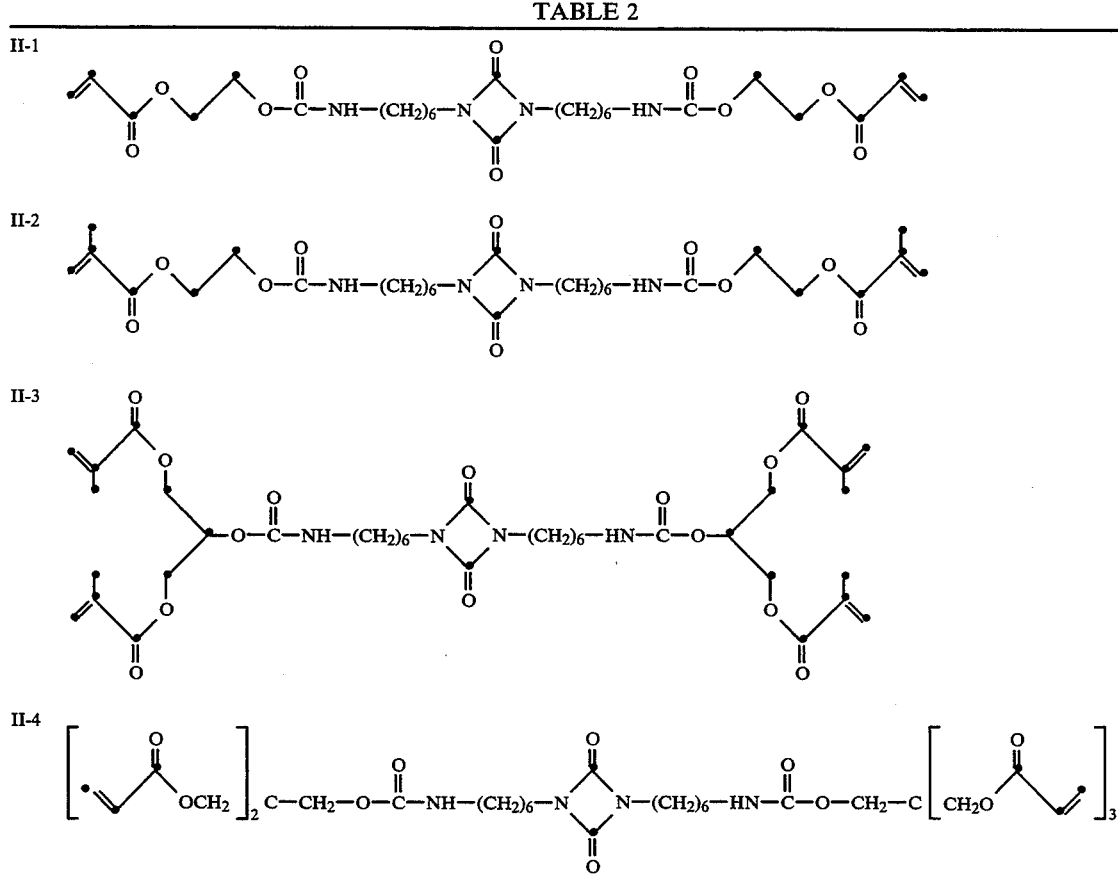

TABLE 2-continued

II-5

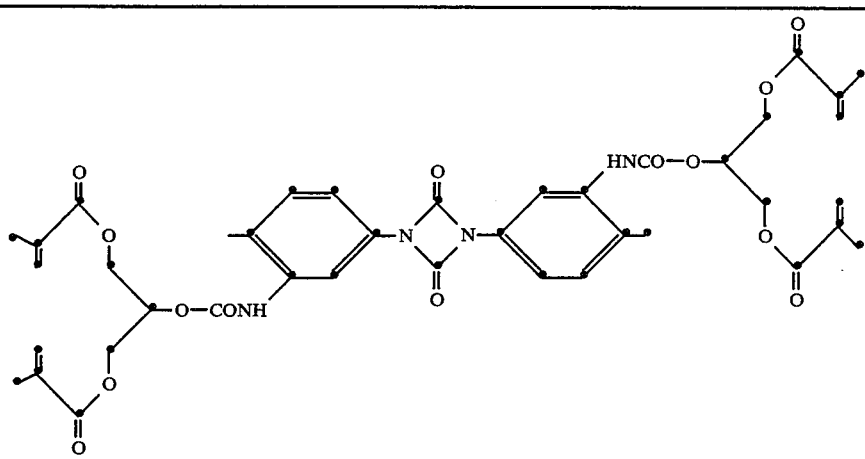

II-6

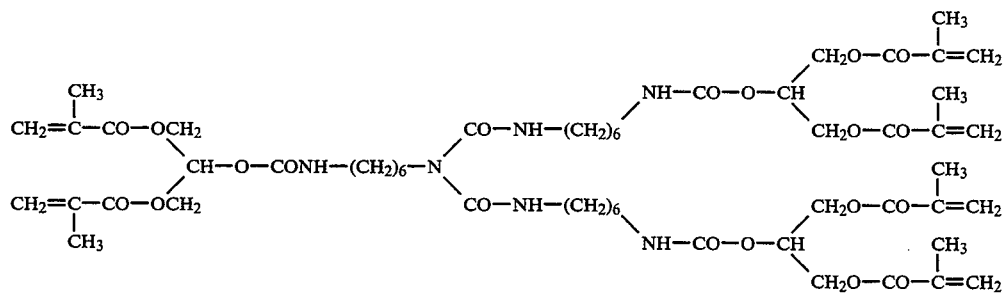

II-7

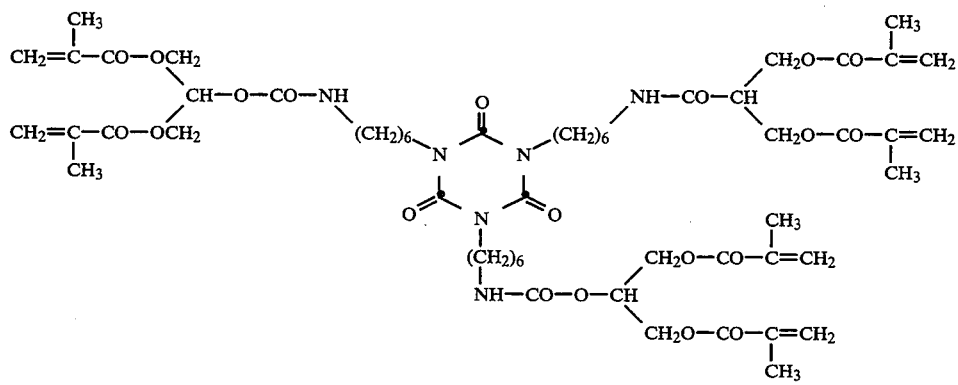

One monomer or a mixture of more than one monomer according to formulas (I) and/or (II) can be used. Further the monomers corresponding to general formula (I) and (II) may be mixed with other polymerizable ethylenically unsaturated compounds. However at least 60% of the polymerizable compounds is preferably made up by the monomers according to the above formulas (I) and (II). Suitable polymerizable ethylenically unsaturated compounds which can be used in accordance with the present invention are e.g. unsaturated esters of polyols, particularly such esters of the alphamethylene carboxylic acids, e.g. ethylene diacrylate, glycerol tri(meth)acrylate, ethylene dimethacrylate, 1,3-propanediol di(meth)acrylate 1,2,4-butanetriol tri(-meth)acrylate, 1,4-cyclohexanediol di(meth)acrylate, 1,4-benzenediol di(meth)acrylate, pentaerythritol tetra(meth)acrylate, 1,5-pentanediol di(meth)acrylate, the bis acrylates and methacrylates of polyethylene glycols of molecular weight 200–500, and the like: unsaturated amides, particularly those of the alphamethylene carboxylic acids, and especially those of alpha-omega-diamines and oxygen-interrupted omega-diamines, such as methylene bis-acrylamide, methylene bis-methacrylamide, 1,6-hexamethylene bis-acrylamide, diethylene triamine tris-methacrylamide, bis(gamma-methacrylamidopropoxy)ethane, beta-methacrylamidoethyl methacrylate, N-(beta-hydroxyethyl)-beta-(methacrylamido)ethyl acrylate and N,N-bis(beta-methacrylolyoxyethyl)acrylamide; vinyl esters e.g. divinyl succinate, divinyl adipate, divinyl phthalate, divinyl butane-1,4-disulfonate; and unsaturated aldehydes, e.g. sorbaldehyde (hexadienal). Other suitable polymerizable ethylenic unsaturated compounds that can be used in accordance with the present invention are polymers and/or oligomers comprising 2 or more polymerizable functions e.g. acrylated epoxies, polyester acrylates, urethane acrylates, polyvinyl alcohol modified with a (meth)acrylic acid or (meth)acrylic acid halide etc.

The total amount of monomer according to formula (I) and/or (II) contained in the imaging element is preferably between 0.2 g/m² and 20 g/m², more preferably between 0.2 g/m² and 10 g/m² and most preferably between 0.4 g/m² and 4 g/m².

Preferably used photoinitiators are polymerization initiators activatable by actinic light and thermally inactive at and below 185° C. Examples of such initiators include the substituted or unsubstituted polynuclear quinones which are compounds having two intracyclic carbonyl groups attached to intracylic carbon atoms in a conjugated six-membered carbocyclic ring, there being at least one aromatic carbocyclic ring fused to the ring containing the carbonyl groups. Such initiators include 9-10-anthraquinone, 1-chloroanthraquinone, 2-chloroanthraquinone, 2-methylanthraquinone, 2-tert-butylanthraquinone, octamethylanthraquinone, 1,4-naphtoquinone, 9,10-phenanthrenequinone, 1-2-benzanthraquinone, 2,3-dichloronaphthoquinone, sodium salt of anthraquinone alpha-sulfonic acid, 3-chloro-2-methylanthraquinone, and 1,2,3,4-tetrahydrobenzene a anthracene-7,12-dione. The photointiators which are also useful are described in Plambeck U.S. Pat. No. 2,760,863 and include vicinal ketaldonyl compounds, such as diacetyl, benzil, etc. alpha-ketaldonyl alcohols, such as benzoin, pivalon, etc. acyloin ethers e.g. benzoin methyl and ethyl ethers, etc.; alpha-hydrocarbon substituted aromatic acyloins, including mehtylbenzoin, alpha-allylbenzoin, and alpha-phenylbenzoin. Still further photoinitiators useful in accordance with the present invention are those disclosed in "Photoreactive Polymers" by Arnost Reiser, "Organic photochemical imaging systems" by G. A. Delzenne, in the paper "UV-Curing Chemistry: Past, Present, and Future" by Christian Decker, published in J. of Coatings Technology, Vol. 59, No 751, August 1987, pages 97–106, in EP-A 362,827, and in U.S. Pat. No. 3,558,309.

As the dye precursors comprised in the imaging element according to the present invention, there are exemplified triarylmethanelactone compounds such as 3,3-bis(p-dimethylaminophenyl)-6-dimethylaminophthalide, 3,3-bis(p-dimethylaminophenyl)phthalide, 3-(p-dimethylaminophenyl)3-(1,2-dimethylindole-3-yl)phthalide, 3-(p-dimethylaminophenyl)-3-(2-methylindole-3-yl)phthalide, 3,3-bis(1,2-dimethylindole-3-yl)-5-dimethylaminophthalide, 3,3-bis(1,2-dimethylindole-3-yl)-6-dimethylaminophthalide, 3,3-bis(9-ethylcarbazole-3-yl)-6-dimethylaminophthalide, 3,3-bis(2-phenylindole-3-yl)-6-dimethylaminophthalide, 3-p-dimethylaminophenyl -3-(1-methylaminophthalide and the like; diphenylmethane compounds such as 4,4-bis-dimethylaminobenzhydryl benzyl ether, N-halophenyl-leucoauramine, N-2,4,5-trichlorophenyl-leucoauramine and the like; thiazine compounds such as benzoyl-leucomethylene bleu, p-nitrobenzoyl-leucomethylene blue and the like; spiro compounds such as 3-methyl-spiro-dinaphthopyran, 3-ethyl-spiro-dinaphthopyran, 3-benzyl-spiro-dinaphthopyran, 3-methyl-naphtho-(6-methoxybenzo)spiropyran, 3-propyl-spiro-dibenzopyran and the like; lactam compounds such as Rhodamine-B anilinelactam, Rhodamine(p-nitroanilino)lactam, Rhodamine(o-chloroanilino)lactam and the like; and fluoran compounds such as 3-dimethylamino-7-methoxyfluoran, 3-diethylamino-6-methoxyfluoran, 3-diethylamino-7-methoxyfluoran, 3-diethylamino-6-methyl-7-chlorofluoran, 3-diethylamino-6,7-dimethylfluoran, 3-(N-ethyl-p-toluidino)-7-methylfluoran, 3-diethylamino-7-N-acetyl-N-methylaminofluoran, 3-diethylamino-7-N-methylaminofluoran, 3-diethylamino7-dibenzylamino-7-N-methyl-N-benzylaminofluoran, 3-diethylamino-7-N-chloroethyl-N-methylaminofluoran, 3-diethylamino-7-N-diethylaminofluoran, 3 - (N-ethyl-p-toluidino)-6-methyl-7-phenylaminofluoran, 3-(N-ethyl-p-toluidino)-6-methyl-7-(p-toluidino)fluoran, 3-diethylamino-6-methyl-7-phenylaminofluoran, 3-di-n-butylaminofluoran, 3-diethylamino-7-(2-carbomethoxyphenylamino)-fluoran, 3-(N-cyclohexyl-N-methylamino)-6-methyl-7-phenylaminofluoran, 3-(N-cyclopentyl-N-methylamino)-6-methyl-7-phenylaminofluoran, 3-(N-cyclopentyl-N-ethylamino)-6-methyl-7-phenylaminofluoran, 3-(N-cyclohexyl-N-ethylamino)-6-methyl-7-phenylaminofluoran, 3-(N-3',3',5'-trimethylcyclohexyl-N-methylamino)-6-methyl -7 -phenylaminofluoran, 3-pyrrolidino-6-methyl-7-phenylaminofluoran, 3-piperidino-6-methyl-7-phenylaminofluoran, 3-diethylamino-6-methyl-7-xylidinofluoran, 3-diethylamino-7-(o-chlorophenylamino)-fluoran, 3-dibutylamino-7-(o-chlorophenylamino)fluoran, 3-pyrrolidino-6-methyl-7-p-butylphenyl aminofluoran, 3-diethylamino-7-(o-fluorophenylamino)fluoran, 3-dibutylamino-7-(o-fluorophenylamino) fluoran, 3-(N-methyl-N-n-amyl)amino-6-methyl -7-phenylaminofluoran, 3-(N-ethyl-N-n-amyl)amino-6-methyl-7-phenylaminofluoran, 3-(N-methyl-N-n-hexyl)amino-6-methyl-7-phenylaminofluoran, 3-(N-ethyl-N-n-hexyl)amino-6-methyl-7-phenylaminofluoran, 3-(N-ethyl-N-6-ethylhexyl)-amino-6-methyl-7-phenylaminofluoran, 3-(N-ethyl-N-tetrahydrofurfurylamino)-6-methyl-7-phenylfluoran and the like. Still further dye precursors for use in connection with the present invention are disclosed in e.g. U.S. Pat. No. 4,803,148, EP-A-302529, DE-A-3.807.744, DE-A-3.942.227, DE-A-3.810.207, U.S. Pat No. 4,753,759 and the references cited therein. The dye precursors may be used either solely or in combination.

Among the color developers, there are many acidic compounds which develop a color by contacting with the above dye precursors, for example, phenolic compounds such as 4-tert-butylphenol, α-naphthol, β-naphtol, 4-acetylphenol, 4-phenylphenol, hydroquinone, 4,4'-isopropylidenediphenol (bisphenol A) , 2,2'-methylenebis(4-chlorophenol), 4,4'-cyclohexylidenediphenol, 4,4'-dihydroxydiphenylsulfide, hydroquinone monobenzyl ether, 4-hydroxybenzophenone, 2,4-dihydroxybenzophenone, 2,4,4'-trihydroxybenzophenone, 2,2',4,4'-tetrahydroxybenzophenone, dimethyl 4-hydroxyphthalate, methyl 4-hydroxybenzoate, ethyl 4-hydroxybenzoate, propyl 4-hydroxybenzoate, sec-butyl 4-hydroxybenzoate, pentyl 4-hydroxybenzoate, phenyl 4-hydroxybenzoate, benzyl 4-hydroxybenzoate, tolyl-4-hydroxybenzoate, chlorophenyl 4-hydroxybenzoate, phenylpropyl 4-hydroxybenzoate, phenetyl 4-hydroxybenzoate, p-chlorobenzyl 4-hydroxybenzoate, p-methoxybenzyl 4-hydroxybenzoate, novolak phenol resin, phenolpolymers and the like; aromatic carboxylic acids such as benzoic acid, p-tert-butylbenzoic acid, trichlorobenzoic acid, terephthalic acid, 3-sec-butyl-4-hydroxybenzoic acid, 3-cyclohexyl-4-hydroxybenzoic acid, 3,5-dimethyl-4-hydroxybenzoic acid, salicylic acid, 3-isopropylsalicylic acid, 3-benzylsalicylic acid, 3-(α-methylbenzyl)salicylic acid, 3-chloro-5-(α-methylbenzyl)salicylic acid, 3,5-di-tert-butylsalicylic acid, 3-phenyl-5-(α,α-dimethylbenzyl)salicylic acid, 3,5-di(α-methylbenzyl)salicylic acid and the like; and salts of the above phenolic compounds or aromatic carboxylic acids with polyvalent metals such as zinc, magnesium, aluminum, calcium, titanium, manganese, tin and nickel.

There can further be used 4-hydroxydiphenylsulfone derivatives such as 4,4'-dihydroxydiphenylsulfone, 3,3'- dipropenyl-4,4'-dihydroxydiphenylsulfone, 4-hydroxy-4'-chlorodiphenylsulfone, 4-hydroxy-4'-methyldiphenylsulfone, 4-hydroxy-3',4'-dimethyldiphenylsulfone, 4-hydroxy-4'-ethyldiphenylsulfone, 4-hydroxy-4'-tert-butyldiphenylsulfone, 4-hydroxy-4'-n-octyldiphenylsulfone, 4-hydroxy-4'-n-octyldiphenylsulfone, 4-hydroxy-4'-methoxydiphenylsulfone, 4-hydroxy-4'-ethoxydiphenylsulfone, 4-hydroxy-4'-isopropyloxydiphenylsulfone, 4-hydroxy-4'-n-butoxydiphenylsulfone, 4-hydroxy-4'-tert-butoxydiphenylsulfone, 4-hydroxy-4'-isoamyloxydiphenylsulfone, 4-hydroxy-4'-n-octyloxydiphenylsulfone, 4-hydroxy-4'-benzyloxydiphenylsulfone, 4-hydroxy-4'-phenoxydiphenylsulfone, 3',4'-trimethylene-4'-hydroxydiphenylsulfone, 3',4'-trimethylene-2,6-dimethyl-4-hydroxydiphenylsulfone, 3',4'-tetramethylene-4-hydroxydiphenylsulfone, 3',4'-tetramethylene-2-methyl-4hydroxydiphenylsulfone and the like.

4-hydroxybenzenesulfonylnaphthalenes may be used as color developers. They include 1-(4-hydroxybenzenesulfonyl)naphthalene, 1-(4-hydroxybenzenesulfonyl)-4-methylnaphthalene, 1-(4-hydroxybenzenesulfonyl)-4-methoxynaphthalene, 1-(4-hydroxybenzenesulfonyl)-4-chloronaphthalene, 1-(4-hydroxy-2-methylbenzenesulfonyl)naphthalene, 1-(4-hydroxy-2-chlorobenzenesulfonyl)naphthalene, 1-(4-hydroxybenzenesulfonyl)-2,-dimethylnaphthalene, 1-(4-hydroxybenzenesulfonyl)-4-hydroxynaphthalene, 1-(4-hydroxybenzenesulfonyl)-2-hydroxynaphthalene, 1-(4-hydroxy-2-isopropylbenzenesulfonyl)naphthalene, 1-(4hydroxy-2-isoamylbenzenesulfonyl)naphthalene, 1-(4- hydroxy-2-isopropyloxybenzenesulfonyl)-naphthalene, 1-(4-hydroxybenzenesulfonyl)-4-tert-butoxynaphthalene, 1-(4-hydroxy-2-benzyloxybenzenesulfonyl)naphthalene, 1-(4-hydroxy-2-phenoxybenzenesulfonyl)naphthalene, 2-(4-hydroxybenzene sulfonyl)naphthalene and the like.

Halophthalic acid monoesters can also be used. Examples are monomethyl ester, monoethyl ester, monocyclopentyl ester, monoallyl ester, monobenzyl ester, mono-p-methylbenzyl ester, mono-p-chlorobenzyl ester, monophenethyl ester, monophenyl ester, mono-p-methylphenyl ester, mono-2,4-dimethylphenyl ester, mono-p-chlorophenyl ester, mono-p-ethoxyphenyl ester, mono-1-naphthyl ester, mono-2-naphthyl ester, mono-2-hydroxyethyl ester, mono-2-hydroxybutyl ester, mono-3-hydroxybutyl-2-ester, mono-2-(2-hydroxyethoxy)ethyl ester, mono-2-hydroxypropyl ester, mono-4-hydroxybutenyl ester, mono-4-hydroxybutyl ester, mono-2-hydroxycyclohexyl ester, mono-4-hydroxycyclohexyl ester and mono-2,3-dihydroxypropyl ester of halophthalic acids, such as 4 (or 5)-fluorophthalic acid, 4 (or 5)-chlorophthalic acid, 4 (or 5)-bromophthalic acid, 3,6 (or 4,5)-dicholorophthalic acid, 3,6 (or 4,5)-dibromophthalic acid, 3,4,5,6-tetrafluorophthalic acid, 3,4,5,6,-tetra chloropthalic acid, 3,4,5,6tetrabromophthalic acid and the like. Among the polyvalent metal compounds which form polyvalent metal salts with the above esters, there are included magnesium, calcium, barium, zinc, aluminum, tin, iron, cobalt, nickel and the like. Preferable metals are magnesium, calcium, barium and zinc.

Further suitable color developers are disclosed in e.g. U.S. Pat. No. 4,803,148, EP-A-302529, DE-A-3.807.744, DE-A-3.942.227, DE-A-3.810.207, U.S. Pat. No. 4,753,759 and the references cited therein.

According to the most preferred embodiment of the present invention the dye precurs or and color developer are arranged in separate layers on the support of the imaging element. As binders for these layers there can be used e.g. polyesters, polyamides, e.g. N-methoxymethyl polyhexamethylene adipamide, vinylidene chloride copolymers, e.g. vinylidene chloride/acrylonitrile, vinylidene chloride/methylacrylate and vinylidene chloride/vinylacetate copolymers etc., ethylene/vinyl acetate copolymers, cellulosic ethers, e.g. methylcellulose, ethyl cellulose and benzyl cellulose, polyethylene, synthetic rubbers, e.g. butadiene/acrylonitrile copolymers, and chloro-2-butadiene-1,3-polymers, cellulose esters, e.g. cellulose acetate, cellulose acetate succinate and cellulose acetate butyrate, cellulose nitrate, polyvinyl esters, e.g. polyvinyl acetate/acrylate, polyvinyl acetate/methacrylate and polyvinyl acetate, polyacrylate and alpha-alkyl polyacrylate esters, e.g. polymethyl methacrylate and polyvinyl acetate, high molecular weight polyethylene oxides of polyglycols having average molecular weights from about 4,000 to 1,000,000, polyvinyl chloride and copolymers, e.g. polyvinyl chloride/acetate, polyvinylchloride/acetate/alkohol, polyvinyl acetal, e.g. polyvinyl butyral, polyvinyl formal, polyformaldehydes, polyurethanes and copolymers, polycarbonate and copolymers, polystyrenes and copolymers e.g. polystyrene/acrylonitrile, Polystyrene/acrylonitrile/butadiene, polyvinyl alcohol, cellulose, anhydrous gelatin, phenolic resins and melamine-formaldehyde resins etc., or mixtures of one ore more of the above polymers.

The layer containing the dye precursor will be preferably free of polymers containing acid groups and phenolic groups. It is further preferred that the softening temperature of both layers is well above ambient temperature, preferably above 40° C. and more preferably above 60° C. The layers containing the dye precursor or color developer can also contain immiscible polymeric or non-polymeric organic or inorganic fillers or reinforcing agents which are essentially colorless e.g. the organophilic silicas, bentonites, silica, powdered glass, $TiO_2$, $ZnO_2$ etc.

Suitable supports for the imaging element in connection with the present invention are supports that are stable at the heating temperatures used for image-wise or overall heating the imaging element in accordance with one of the above described methods. Examples of useful supports are e.g. polyester film supports e.g. polyethylene terephthalate, glass, wood, paper, polyethylene coated paper, cellulose esters e.g. cellulose acetate, cellulose propionate, cellulose butyrate, polycarbonate, polyvinyl chloride, polyimide, polypropylene etc.

According to a variant of the most preferred embodiment of the present invention there can be provided a so-called barrier layer between the layers containing respectively the dye precursor and color developer. Such barrier layer will help improving the stability of the image by further separating the dye precursor from the color developer. Preferably such barrier layer will have a softening and or melting temperature above 30° C. and more preferably above 40° C.

Said barrier layer may also contain a photopolymerizable composition containing a polymerizable compound e.g. one or more monomers, oligomers or polymers with polymerizable groups, or mixtures thereof and optionally a photoinitiator. Suitable polymerizable compounds that can be included in said barrier layer are e.g. monomers according to formula (I) or (II) or polymerizable compounds as listed above. A suitable photoinitiator is e.g. one of the photoinitiators listed above. It will further be clear to someone skilled in the art that said barrier layer can also be used in conjunction with a dye precursor layer and color developer layer that do not comprise a polymerizable compound.

The imaging element according to the invention may include further additional layers such as e.g. a surface layer for protecting the imaging element against wear and scratches or subbing layers for improving the adhesion of the layers contained in the imaging element to its support.

The present invention is illustrated by the following examples without however limiting it thereto. All parts are by weight unless otherwise specified.

EXAMPLES

The following coating solutions were used in the examples:

| Coating solutions for the dye precursor layer: | |
|---|---|
| Coating solution A (methylethylketone): | |
| polyvinylbutyral (Butvar B79 obtained from Monsanto) | 1.25% |
| compound II-7 of table 2 above | 1.25% |
| leuco dye L-1 (see below) | 5.00% |
| Irgacure 651 (obtained from Ciba-Geigy) | 0.25% |
| Coating solution B (methylethylketone): | |
| copolymer of vinylidene chloride and vinylacetate | 1.25% |
| compound II-7 of table 2 above | 1.25% |
| leuco dye L-1 (see below) | 4.00% |
| Irgacure 651 (obtained from Ciba-Geigy) | 0.25% |
| Coating solution C (methylethylketone): | |
| copolymer of vinylidene chloride and vinylacetate | 2.5% |
| leuco dye L-1 (see below) | 4.00% |
| Coating solution D (methylethylketone): | |
| copolymer of vinylidene chloride and vinylacetate | 1.25% |
| trimethylolpropanetriacrylate | 1.25% |
| leuco dye L-1 (see below) | 4.00% |
| Irgacure 651, (obtained from Ciba-Geigy) | 0.25% |
| Coating solution E (methylethylketone): | |
| copolymer of vinylidene chloride and vinylacetate | 1.25% |
| pentaerythritoltetra-acrylate | 1.25% |
| leuco dye L-1 (see below) | 4.00% |
| Irgacure 651 (obtained from Ciba-Geigy) | 0.25% |
| Coating solution F (methylethylketone): | |
| copolymer of vinylidene chloride and vinylacetate | 1.25% |
| compound II-7 of table 2 | 1.25% |
| leuco dye L-2 (see below) | 4.00% |
| Irgacure 651 (obtained from Ciba-Geigy) | 0.25% |
| Coating solutions for the color developer layer: | |
| Coating solution G (methylethylketone): | |
| color developer C-1 (see below) | 4% |
| polyvinylbutyral (Butvar B79 obtained from Monsanto) | 4% |
| Coating solution H (methylethylketone): | |
| polyvinylbutyral (Butvar B79 obtained from Monsanto) | 2% |
| compound II-7 of table 2 | 2% |
| color developer C-1 (see below) | 4% |
| Irgacure 651 (obtained from Ciba-Geigy) | 0.3% |
| Coating solution K (methylethylketone): | |
| copolymer of vinylidene chloride and vinylacetate | 4% |
| color developer C-2 (see below) | 4% |

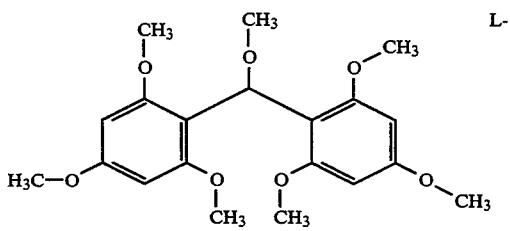

L-1

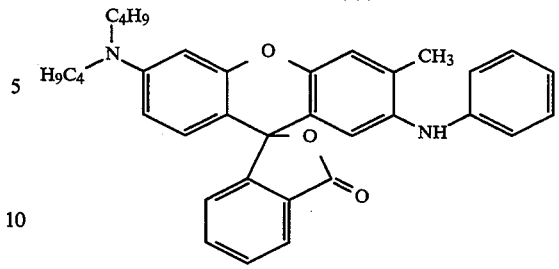

L-2 formulas of the color developers used:

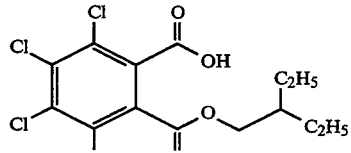

C-1

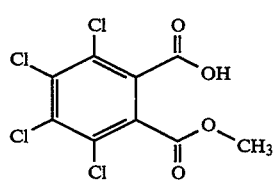

C-2

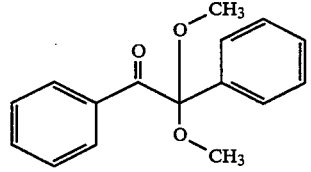

Preparation of the samples:

Sample 1:

On a polyethyleneterephthalate support having a thickness of 63 μm were applied in the order given coating solution A and coating solution H to a wet thickness of 50 μm each, Both layers were then covered with a polyethylene terephthalate film of 5 μm thickness, Sample 2:

Sample 2 was prepared similar to sample 1 with the exception that an intermediate layer was applied from an aqueous coating solution containing 4% of polyvinylalcohol of which 25% of the hydroxy groups were reacted with methacryloyl chloride to a wet thickness of 10 μm.

Sample 3:

Sample 3 was prepared similar to sample 2 with the exception that a 2% solution of said modified polyvinylalcohol was used, Sample 4:

Sample 4 was prepared similar to sample 2 with the exception that a 1% solution of said modified polyvinylalcohol was used.

Sample 5:

Sample 5 was prepared similar to sample 1 with the exception that coating solution H was replaced with coating solution G.

Sample 6:

Sample 6 was prepared similar to sample 3 with the exception that coating solution A and H were replaced by coating solutions F and K respectively.

Sample 7:

Sample 7 was prepared similar to sample 6 with the exception that coating solution F was replaced with coating solution B, Sample 8:

Sample 8 was prepared similar to sample 6 with the exception that coating solution F was replaced with coating solution C, Sample 9:

Sample 9 was prepared similar to sample 6 with the exception that coating solution F was replaced with coating solution E, Sample 10:

Sample 10 was prepared similar to sample 6 with the exception that coating solution F was replaced with coating solution D, Evaluation:

Each of the samples was imaged with a thermal head in a Hitachi VY 100 videoprinter, The density in the image-areas ($D_{max}$) and non-image areas ($D_{min}$) of each of the obtained images was then measured, Part of each image was then heated for 30s (sample 1 to 5) or 60s (sample 6 to 10) at 75° C. and the above mentioned density values were again measured, The other part of the image was overall exposed to UV irradiation and the above mentioned density values were again measured, Finally the latter image part was heated as described above and density values were measured, The obtained results are shown in the following table:

TABLE 3

| sample | not irradiated* | | irradiated with UV* | |
|---|---|---|---|---|
| | $D_{max}$ | $D_{min}$ | $D_{max}$ | $D_{min}$ |
| 1 | 1.24/1.15 | 0.10/0.36 | 1.24/1.19 | 0.12/0.06 |
| 2 | 1.03/0.95 | 0.07/0.21 | 0.97/0.99 | 0.12/0.09 |
| 3 | 1.10/0.98 | 0.10/0.32 | 1.05/1.01 | 0.12/0.06 |
| 4 | 1.15/1.15 | 0.14/0.28 | 1.11/1.09 | 0.09/0.11 |
| 5 | 1.20/1.07 | 0.11/0.34 | 1.25/1.17 | 0.07/0.08 |
| 6 | 0.97/0.95 | 0.10/0.45 | 0.89/0.91 | 0.07/0.16 |
| 7 | 2.05/1.94 | 0.11/0.47 | 2.01/1.98 | 0.14/0.17 |
| 8 | 1.95/1.98 | 0.15/0.56 | 1.98/1.99 | 0.11/0.49 |
| 9 | 1.95/1.80 | 0.10/0.45 | 2.03/2.06 | 0.14/0.34 |
| 10 | 2.17/2.04 | 0.14/0.53 | 2.11/2.09 | 0.20/0.46 |

*values left to the slash are before heat treatment at 75° C. and the values right to the slash are those obtained after heat treatment at 75° C.

From the above table it can be seen that the images obtained with the samples according to the invention (samples 1 to 7) can be efficiently stabilized against temperature increase when overall exposed to UV irradiation whereas the comparative samples 8 (not containing a monomer) and samples 9 and 10 do not show or hardly show an improvement of the temperature stability of the image upon overall exposure of the image to UV irradiation.

We claim:

1. An imaging element comprising on a support a dye precursor and a color developer which are heat reactable and arranged in the same layer or in separater layers characterized in that a monomer according to one of formulas (I) or (II) and a photoinitiator is present in a layer containing said dye precursor and/or color developer:

(I)

wherein n represents an integer from 1 to 3, m equals an integer of 3 to 6 when n equals 1, and 2 to 6 when n equals 2 or 3, and u equals 0 or 1; A represents an organic group of the following nature being 3 to 6 valent when n equals 1 and being 2 to 6 valent when n equals 2 or 3:

a) a hydrocarbon residue containing 5 to 25 carbon atoms which may be interrupted by one or more ether, ester or amide functions;

b) 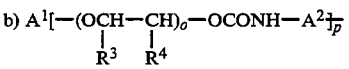

with $A^1$ representing a linear or branched aliphatic residue that may contain 0 to 3 0-atoms and 2 to 20 C-atoms, an aromatic residue containing 6 to 24 carbon atoms, an aromatic aliphatic residue containing 7 to 28 C-atoms or an cycloaliphatic residue containing 6 to 26 C-atoms, $R^3$ and $R^4$ each independently representing a hydrogen or a methyl group, $A^2$ representing an aromatic, aliphatic or cycloaliphatic hydrocarbon residue containing 5 to 25 carbon atoms, o represents an integer of 0 to 5 and p represents an integer of 2 to 6 when n equals 2 or 3 and represents an integer of 3 to 6 when n equals 1;

c) 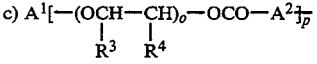

wherein $A^1$, $A^2$, $R^3$, $R^4$, and p have the same meaning as defined above d) 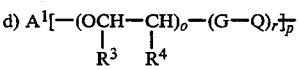

wherein $A^1$, $R^3$, $R^4$, and p have the same meaning as defined above;

G represents $-O-CO-NH-Y(-COO-)_q-$;

wherein Y represents a divalent (cyclo)aliphatic residue containing 2 to 15 C-atoms and that may contain an ester, ether or urethane function, and q represents 0 or 1

Q represents a linear or branched aliphatic hydrocarbon residue containing 3 to 15 carbon atoms and which may comprise 1 to 3 oxygen bridges and r equals 0 or 1, X represents O or $NR^2$, $L^1$ represents an aliphatic hydrocarbon residue that is at least divalent and that may comprise 1 to 3 0-atoms, $L^2$ represents a lower alkylene of 1 to 6 C-atoms which may be branched or linear, $R^1$ represents hydrogen or a methyl group, $R^2$ represents hydrogen or a lower alkyl group of 1 to 6 C-atoms;

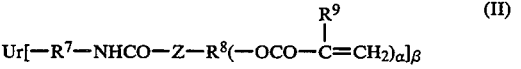

(II)

wherein

Ur represents a divalent or trivalent condensed urea residue;

Z represents 0 or NR$^{10}$ with R$^{10}$ representing alkyl containing 1 to 12 C-atoms;

R$^7$ represents a divalent hydrocarbon residue containing 2 to 25 C-atoms;

R$^8$ represents a hydrocarbon residue with a valence between 2 and 6, and containing 2 to 18 C-atoms, which can be linear or branched and which can be interrupted by up to 3 0 atoms;

R$^9$ represents hydrogen or methyl;

α represents an integer from 1 to 5, and

β equals 2 or 3.

2. An imaging element according to claim 1 wherein A and/or A$^2$ in said formula (I) corresponds to one of the following formulas:

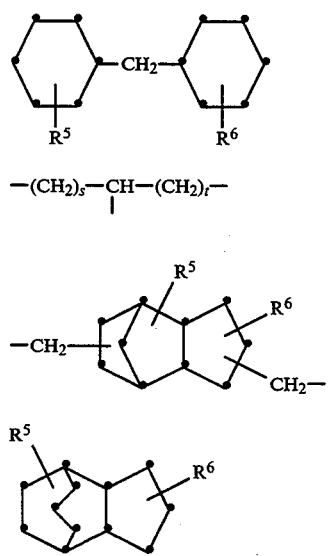

wherein R$^5$ and R$^6$ each independently represent hydrogen or a lower alkyl of 1 to 6 C-atoms, s and t independently represent an integer from 1 to 6 and wherein the aliphatic hydrocarbon residues Ia, Ic and Id comprise 2 to 6 free valences.

3. An imaging element according to claim 1 wherein the urea residue represented by Ur corresponds to one of the following structural units:

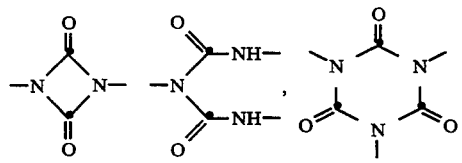

4. An imaging element according to claim 1 wherein said dye precursor and color developer are arranged in separate layers and wherein said monomer according to formulas (I) or (II) is comprised in the layer containing said dye precursor.

5. An imaging element according to claim 1 wherein said dye precursor and color developer are arranged in separate layers and wherein said monomer according to formulas (I) or (II) is comprised in the layer containing said color developer.

6. An imaging element according to claim 4 wherein there is provided a barrier layer between the layer containing said dye precursor and the layer containing said color developer.

7. An imaging element according to claim 6 wherein said barrier layer comprises one or more compounds having a polymerizable group.

8. A method for obtaining an image comprising image-wise exposing an imaging element comprising on a support a dye precursor and a color developer which are heat reactable and arranged in the same layer or in separate layers characterized in that a monomer according to one of formulas (I) or (II) and a photoinitiator is present in a layer containing said dye precursor and/or color developer:

wherein n represents an integer from 1 to 3, m equals an integer of 3 to 6 when n equals 1, and 2 to 6 when n equals 2 or 3, and u equals 0 or 1;

A represents an organic group of the following nature being 3 to 6 valent when n equals 1 and being 2 to 6 valent when n equals 2 or 3:

a) a hydrocarbon residue containing 5 to 25 carbon atoms which may be interrupted by one or more ether, ester or amide functions;

b) A$^1$[—(OCH—CH)$_o$—OCONH—A$^2$]$_p$
          |       |
          R$^3$   R$^4$ with A$^1$ representing a linear or branched aliphatic residue that may contain 0 to 3 0-atoms and 2 to 20 C-atoms, an aromatic residue containing 6 to 24 carbon atoms, an aromatic aliphatic residue containing 7 to 28 C-atoms or an cycloaliphatic residue containing 6 to 26 C-atoms, R$^3$ and R$^4$ each independently representing a hydrogen or a methyl group, A$^2$ representing an aromatic, aliphatic or cycloaliphatic hydrocarbon residue containing 5 to 25 carbon atoms, o represents an integer of 0 to 5 and p represents an integer of 2 to 6 when n equals 2 or 3 and represents an integer of 3 to 6 when n equals 1;

c) 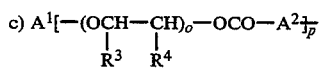

wherein A$^1$, A$^2$, R$^3$, R$^4$, o and p have the same meaning as defined above d) 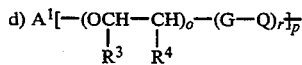

wherein A$^1$, R$^3$, R$^4$, o and p have the same meaning as defined above;

G represents —O—CO—NH—Y(—COO—)$_q$—;

wherein Y represents a divalent (cyclo)aliphatic residue containing 2 to 15 C-atoms and that may contain an ester, ether or urethane function, and q represents 0 or 1

Q represents a linear or branched aliphatic hydrocarbon residue containing 3 to 15 carbon atoms and which may comprise 1 to 3 oxygen bridges and r equals 0 or 1, X represents 0 or NR$^2$, L¹ represents an aliphatic hydrocarbon residue that is at least divalent and that may comprise 1 to 3 0-atoms, L² represents a lower alkylene of 1 to 6 C-a-toms which may be branched or linear, R¹ represents hydrogen or a methyl group, R² represents hydrogen or a lower alkyl group of 1 to 6 C-atoms;

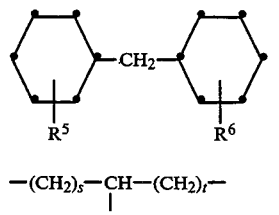

(II)

wherein
- Ur represents a divalent or trivalent condensed urea residue;
- Z represents 0 or $NR^{10}$ with $R^{10}$ representing alkyl containing 1 to 12 C-atoms;
- $R^7$ represents a divalent hydrocarbon residue containing 2 to 25 C-atoms;
- $R^8$ represents a hydrocarbon residue with a valence between 2 and 6, and containing 2 to 18 C-atoms, which can be linear or branched and which can be interrupted by up to 3 0 atoms;
- $R^9$ represents hydrogen or methyl;
- α represents an integer from 1 to 5, and
- β equals 2 or 3, to actinic readiation and subsequently or simultaneously overall exposing said imaging element to heat.

9. A method according to claim 8 wherein A and/or $A^2$ in said formula (I) corresponds to one of the following formulas:

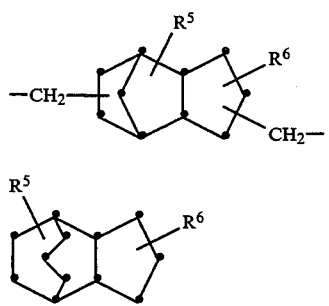

wherein $R^5$ and $R^6$ each independently represent hydrogen or a lower alkyl of 1 to 6 C-atoms, s and t independently represent an integer from 1 to 6 and wherein the aliphatic hydrocarbon residues Ia, Ic and Id comprise 2 to 6 free valences.

10. A method for obtaining an image comprising image-wise exposing an imaging element-comprising on a support a dye precursor and a color developer which are heat reactable and arranged in the same layer or in separate layers characterized in that a monomer according to one of formulas (I) or (II) and a photoinitiator is present in a layer containing said dye precursor and/or color developer:

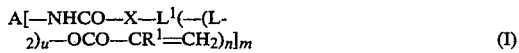

(I)

wherein n represents an integer from 1 to 3, m equals an integer of 3 to 6 when n equals 1, and 2 to 6 when n equals 2 or 3, and u equals 0 or 1; A represents an organic group of the following nature being 3 to 6 valent when n equals 1 and being 2 to 6 valent when n equals 2 or 3:

a) a hydrocarbon residue containing 5 to 25 carbon atoms which may be interrupted by one or more ether, ester or amide functions;

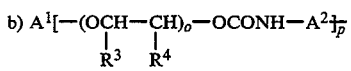

with $A^1$ representing a linear or branched aliphatic residue that may contain 0 to 3 0-atoms and 2 to 20 C-atoms; an aromatic residue containing 6 to 24 carbon atoms, an aromatic aliphatic residue containing 7 to 28 C-atoms or an cycloaliphatic residue containing 6 to 26 C-atoms, $R^3$ and $R^4$ each independently representing a hydrogen or a methyl group, $A^2$ representing an aromatic, aliphatic or cycloaliphatic hydrocarbon residue containing 5 to 25 carbon atoms, o represents an integer of 0 to 5 and p represents an integer of 2 to 6 when n equals 2 or 3 and represents an integer of 3 to 6 when n equals 1;

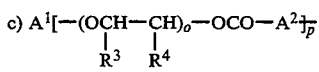

wherein $A^1$, $A^2$, $R^3$, $R^4$, o and p have the same meaning as defined above

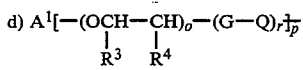

wherein $A^1$, $R^3$, $R^4$, o and p have the same meaning as defined above;

G represents $-O-CO-NH-Y(-COO-)_q-$;

wherein Y represents a divalent (cyclo)aliphatic residue containing 2 to 15 C-atoms and that may contain an ester, ether or urethane function, and q represents 0 or 1

Q represents a linear or branched aliphatic hydrocarbon residue containing 3 to 15 carbon atoms and which may comprise 1 to 3 oxygen bridges and r equals 0 or 1, X represents 0 or $NR^2$, L¹ represents an aliphatic hydrocarbon residue that is at least divalent and that may comprise 1 to 3 0-atoms, L² represents a lower alkylene of 1 to 6 C-atoms which may be branched or linear, R¹ represents hydrogen or a methyl group, R² represents hydrogen or a lower alkyl group of 1 to 6 C-atoms;

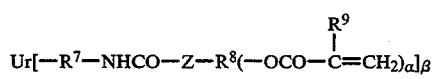 (II)

wherein
- Ur represents a divalent or trivalent condensed urea residue;
- Z represents O or $NR^{10}$ with $R^{10}$ representing alkyl containing 1 to 12 C-atoms;
- $R^7$ represents a divalent hydrocarbon residue containing 2 to 25 C-atoms;
- $R^8$ represents a hydrocarbon residue with a valence between 2 and 6, and containing 2 to 18 C-atoms, which can be linear or branched and which can be interrupted by up to 3 O atoms;
- $R^9$ represents hydrogen or methyl;
- $\alpha$ represents an integer from 1 to 5, and
- $\beta$ equals 2 or 3, to heat and subsequently or simultaneously overall exposing said imaging element to actinic radiation.

11. A method according to claim 10 wherein A and/or $A^2$ in said formula (I) corresponds to one of the following formulas:

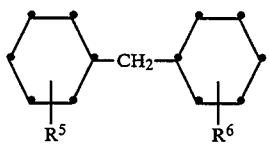 Ia

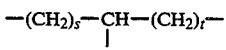 Ib

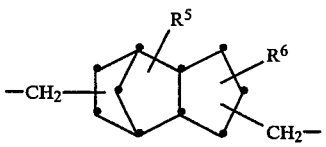 Ic

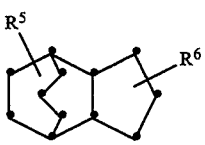 Id wherein $R^5$ and $R^6$ each independently represent hydrogen or a lower alkyl of 1 to 6 C-atoms, s and t independently represent an integer from 1 to 6 and wherein the aliphatic hydrocarbon residues Ia, Ic and Id comprise 2 to 6 free valences.

12. A method according to claim 10 wherein said image-wise exposure to heat is carried out by means of a thermal head.

* * * * *

UNITED STATES PATENT AND TRADEMARK OFFICE
CERTIFICATE OF CORRECTION

PATENT NO. : 5,395,737
DATED : March 7, 1995
INVENTOR(S) : Wolfgang Podszun et al It is certified that error appears in the above-indentified patent and that said Letters Patent is hereby corrected as shown below:

Column 7, Formula 18, first part should read --

Column 9, Formula II-4, first part should read --

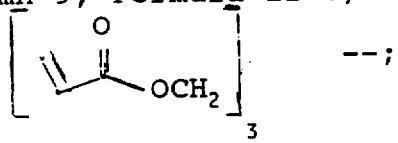

Column 15, line 17 "methyl-4hydroxydiphenylsulfone" should read -- methyl-4-hydroxydiphenylsulfone --;

Column 15, line 56, "3,4,5,6tetrabromophthalic" should read -- 3,4,5,6-tetrabromophthalic --;

Column 15, line 67, "dye precurs" should read -- dye precursor --;

Column 16, line 25, "Polystyrene" should read --polystyrene--;

Column 19, line 20, "coating solution D," should read -- coating solution D. --;

Column 19, line 33, "were measured," should read -- were measured. --;

Column 20, line 35, "$A^1$, $A^2$, $R^3$, $R^4$, and p" should read -- $A^1$, $A^2$, $R^3$, $R^4$, o and p --;

UNITED STATES PATENT AND TRADEMARK OFFICE
CERTIFICATE OF CORRECTION

PATENT NO. : 5,395,737
DATED : March 7, 1995
INVENTOR(S) : Wolfgang Podszun et al It is certified that error appears in the above-indentified patent and that said Letters Patent is hereby corrected as shown below:

Column 20, line 43, "$A^1, R^3, R^4,$ and p" should read -- $A^1, R^3, R^4,$ o and p --;

Column 23, line 4, "1 to 6 C-a-toms" should read -- 1 to 6 C-atoms --.

Signed and Sealed this

Thirty-first Day of October 1995

Attest:

BRUCE LEHMAN

Attesting Officer

Commissioner of Patents and Trademarks